(12) United States Patent
Nguyen

(10) Patent No.: US 11,607,491 B2
(45) Date of Patent: Mar. 21, 2023

(54) INFUSION PUMP WITH PROGRAM KEY

(71) Applicant: Becton, Dickinson and Company, Franklin Lakes, NJ (US)

(72) Inventor: Tony Nguyen, Hopkinton, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 91 days.

(21) Appl. No.: 15/118,837

(22) PCT Filed: Feb. 12, 2015

(86) PCT No.: PCT/US2015/015598
§ 371 (c)(1),
(2) Date: Aug. 12, 2016

(87) PCT Pub. No.: WO2015/126721
PCT Pub. Date: Aug. 27, 2015

(65) Prior Publication Data
US 2017/0049960 A1    Feb. 23, 2017

Related U.S. Application Data

(60) Provisional application No. 61/943,718, filed on Feb. 24, 2014.

(51) Int. Cl.
*A61M 5/172* (2006.01)
*A61M 5/142* (2006.01)
(Continued)

(52) U.S. Cl.
CPC .......... *A61M 5/172* (2013.01); *A61M 5/1413* (2013.01); *A61M 5/14248* (2013.01);
(Continued)

(58) Field of Classification Search
CPC ................ A61M 5/1413; A61M 5/142; A61M 5/14208; A61M 5/14244; A61M 5/14248;
(Continued)

(56) References Cited

U.S. PATENT DOCUMENTS 7,727,180 B2 *  6/2010  Jacobsen ........... A61M 5/14244
                                                    604/65
2005/0177108 A1    8/2005  Paul et al.
(Continued)

FOREIGN PATENT DOCUMENTS

JP    2003527217 A    9/2003
JP    2013503692 A    2/2013
(Continued)

*Primary Examiner* — Shefali D Patel
(74) *Attorney, Agent, or Firm* — Dickinson Wright PLLC

(57) ABSTRACT

A wearable infusion pump allows a user to insert a program key into a housing of the pump to select a continuous dosage rate. Program keys are shaped to close contacts on a printed circuit board within the housing to communicate the selected dosage rate to a microprocessor. In this way, a single disposable pump, sold with one Stock keeping unit (SKU), can be used to deliver a plurality of dosage rates. The disposable pump is provided with an on-board display and a one-button on-board user operable control. In preferred embodiments, the infusion pump according to the invention may be used for continuous delivery of insulin in management of Type II diabetes.

19 Claims, 3 Drawing Sheets

(51) Int. Cl.
*A61M 5/168* (2006.01)
*A61M 5/14* (2006.01)
*A61M 5/145* (2006.01)

(52) U.S. Cl.
CPC ....... *A61M 5/16877* (2013.01); *A61M 5/1452* (2013.01); *A61M 2005/14208* (2013.01); *A61M 2005/14252* (2013.01); *A61M 2205/12* (2013.01); *A61M 2205/50* (2013.01); *A61M 2205/502* (2013.01); *A61M 2205/587* (2013.01); *A61M 2205/6018* (2013.01); *A61M 2205/6036* (2013.01); *A61M 2205/6045* (2013.01)

(58) Field of Classification Search
CPC ......... A61M 2005/14252; A61M 2005/14256; A61M 2005/1426; A61M 2005/14268; A61M 2005/1585; A61M 2005/1587; A61M 5/16877; A61M 5/172; A61M 2205/50; A61M 2205/502; A61M 2205/587; A61M 2205/6018; A61M 2205/6036; A61M 2205/6045; A61M 2205/12; A61M 2205/121; A61M 2205/123; A61M 5/1452

See application file for complete search history.

(56) References Cited

U.S. PATENT DOCUMENTS

| | | |
|---|---|---|
| 2005/0273059 A1 | 12/2005 | Mernoe et al. |
| 2007/0100283 A1* | 5/2007 | Causey, III ......... A61M 5/1456 604/152 |
| 2008/0009787 A1 | 1/2008 | Jacobsen et al. |
| 2010/0168683 A1 | 7/2010 | Cabiri |
| 2011/0054285 A1 | 3/2011 | Searle et al. |
| 2011/0295205 A1* | 12/2011 | Kaufmann ............ A61M 5/158 604/136 |
| 2013/0253465 A1* | 9/2013 | Holtwick ................ A61M 5/19 604/411 |

FOREIGN PATENT DOCUMENTS

| | | |
|---|---|---|
| WO | WO-0170307 A1 | 9/2001 |
| WO | WO-2004093648 A2 | 11/2004 |

* cited by examiner

INFUSION PUMP WITH PROGRAM KEY

CROSS REFERENCE TO RELATED APPLICATIONS

This application is a 371 of PCT/US15/15598, filed Feb. 12, 2015, which claims priority to U.S. 61/943,718, filed Feb. 24, 2014, the disclosures of which are incorporated herein in their entireties.

BACKGROUND OF THE INVENTION

Field of the Invention

The invention is directed to a disposable infusion pump, such as may be used for the continuous delivery of insulin in the treatment of diabetes.

Description of the Related Art

An infusion pump is a device attached to a wearer's body to deliver a medication continuously to a subcutaneous site on the wearer's body. A first type of infusion pump is suitable for a user with Type I diabetes, that is, a patient whose body does not produce native insulin. In this case, the insulin delivery process must be tightly controlled throughout the day, often in conjunction with frequent blood glucose testing, to ensure the user obtains the proper concentration of insulin in the bloodstream. For this purpose, a typical infusion pump system according to the prior art is a two part device which comprises a cannula-bearing infusion set worn on the body, and a programmable handheld controller module, which communicates wirelessly with the infusion set. A second type of infusion pump is purely disposable, intended for the Type II diabetes patient whose native insulin production and regulation is impaired and who prefers fewer features and less complexity than are provided with a Type I pump. The second type of pump is pre-programmed to deliver a continuous dose of insulin over a period of days, usually three-days. The user may have the option to fill the pump and to manually deliver meal time bolus injections with the same device, but this device is not provided with programming means to change the continuous dosage.

Thus one object of the invention is to provide a disposable infusion pump that has selectable continuous rate dosage settings without requiring a wireless controller, and which provides simplified feedback in the form of an on-board display, so as to be suitable for a Type II diabetes patient desiring greater freedom in the processes of administering insulin.

SUMMARY OF THE INVENTION

Thus, in one aspect, the invention pertains to a fluid medication delivery device comprising a wearable infusion pump. The pump contains a housing including an insertion cannula, a medication reservoir in communication with the cannula; an actuator in fluid communication with the reservoir and the cannula; an onboard display; a power source; and a microprocessor operatively communicating with the power source, the on-board display, the insertion cannula, and the actuator.

The infusion pump further includes a program key insert aperture in the housing and one or more program key(s) received in the program key insert aperture. Inserting the program key "wakes up" the device and closes one or more contacts on a printed circuit board within the housing to communicate a dosage rate to the microprocessor.

DETAILED DESCRIPTION OF THE INVENTION

The illustrative embodiments of the invention refer to a wearable infusion pump in which the patient can insert a program key to enable a selectable, pre-set, continuous dosage rate, read real-time status and information from the device via an onboard display, and perform cannula insertion and bolus delivery operations via an onboard control. It is known to provide a wearable infusion pump for Type I diabetes with a handheld device with a wireless transmitter that needs to be programmed by the physician or patient in order to receive the medication dosage. Truly disposable pumps, as may be used to control Type II diabetes, are available for a single continuous dosage regimen. This means that a regimen of 20 insulin units per day, for example, requires a different set of pumps with a different stock keeping unit (SKU), than a set of pumps adapted to deliver 30 units per day.

Figure 1A:
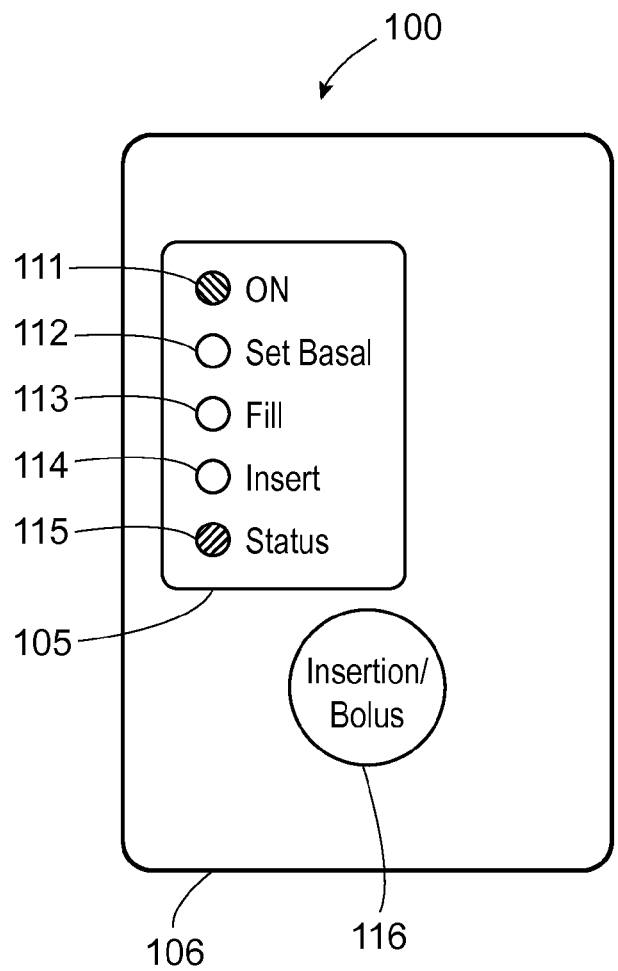
FIG. 1A is a top view of an embodiment of the infusion pump housing comprising the onboard display and separate light-emitting diode indicators.

In FIG. 1A, a wearable infusion pump drug delivery device 100 according to the invention is provided with housing 106 utilizing an onboard display 105. The housing 106 provides the structure that supports the components of the infusion pump described below. The housing 106 is water-tight, preventing mechanical or electrical failure of the inner components resulting from fluid ingress. As the device is meant to be worn continuously on the body without removal for up to three days, the housing 106 is preferably composed of plastic or other lightweight material to prevent the device from becoming heavy or cumbersome on the user's body and includes an adhesive system (not shown) to adhere the device to the user's body.

In the embodiment of FIG. 1A, the onboard display 105 of device 100 has several light-emitting diodes (LEDs) indicating pump status and user prompts. In detail, LED 111 indicates the ON/OFF state of the infusion pump. The user turns the pump on by inserting the appropriate basal rate program key 119-123 in the program key insert aperture/key hole 118 located on the bottom, inferior portion of the pump housing 102. The ON light diode then turns to green indicating a ready state after the user initially inserts the key. To avoid a continuously visible light display on the user's body, the green ON indicator may be adapted to dissipate after a period of time, as known in the art. After the device is switched on with the program key, the SET BASAL diode 112 flashes to green, indicating the microprocessor (MPU) 130 is reading and storing the basal rate programmed by the key (described in connection with FIG. 3). After the basal rate is stored by the pump, a yellow LED on the FILL diode 113 prompts the user to fill reservoir 125 via a fill port 142 in fluid communication with the reservoir. The user fills reservoir 125 and the FILL diode 113 is lit with a green light, indicating the reservoir 125 is adequately filled with medication. Alternatively, the infusion pump may be adapted to accept a pre-filled cartridge with a similar system of prompts.

The disposable pump according to the invention typically can be worn for a period of up to three days. The reservoir 125 thus is capable of storing a volume of equivalent to the highest dose of medication given per day over three days, including meal-time bolus deliveries. The pump is adapted to provide continuous dosages of insulin in a range from 10 U/day to 80 U/day, preferably 20 U/day to 60 U/day. Mealtime bolus delivery generally does not exceed 30-40 U/day. Therefore, the reservoir 125 may hold up to 300-400 units of insulin, for example, according to the maximum amount of medication deliverable over a three-day period. The volume of the reservoir is not a critical feature, but based on this calculation could be 3 to 5 ml.

Any type of fluid delivery system known in the art may be used with the invention, such as a rotary pump in communication with a reservoir 125, or a plunger 126 the like device within the reservoir, which provide pressure in response to actuator 127 to deliver a precise quantity of fluid to the cannula 124. The actuator includes a motor 141 communicating with the microprocessor 130 to ensure that medication is delivered from the reservoir 125 in a calibrated amount.

Once the reservoir 125 is filled by the user, the medication is ready to be delivered through the cannula and inserted in the body. The device may comprise a motor 143 which inserts the cannula into the injection site responsive to a command from MPU 130. The INSERT LED 114 then lights up, indicating the ready stage of the device to deliver medication to the user. At this point, the user can attach the device to the body using the adhesive. The cannula 124 is deployed by the user by depressing the INSERTION/BOLUS button 116. The INSERTION/BOLUS 116 is a single, user-operable button attached to and sealed flush with the outer part of the housing 102 on the anterior portion, facing away from the user's body. It is depressed for two reasons. First, it is used for initial insertion of the cannula 124 into the user's body. The button also acts to provide a bolus delivery of drug, where the user activates a one-time bolus of medication, in addition to the continuous drug delivery, at mealtime for example, as is sometimes required for Type II diabetic patients. Although not limited in this regard, the INSERTION/BOLUS button 116 may be calibrated to deliver 1 to 5 units of insulin with each depression of the button, and would typically cut off after a maximum number of depressions, i.e., a maximum allowable daily bolus delivery may be pre-programmed into the MPU.

The cannula 124 is referred to herein as an "insertion cannula," meaning that the cannula is initially retracted into the housing and can be inserted into the user's subcutaneous space by pressing the INSERT/BOLUS button 116. Apparatus for driving a small cannula of an infusion pump into a user's subcutaneous tissue are known in the art, and may be adapted from available designs. In embodiments, the cannula 124 is located on an infusion set connected to the infusion pump by tubing.

The STATUS 115 button of the onboard display 105 indicates to the user that the amount of insulin in the drug delivery device is low, or if an error condition is found. The STATUS 115 diode will light yellow when there is a low amount of insulin in the device and red when the reservoir 125 is at empty or if there is a device malfunction requiring action by the user.

Figure 1B:
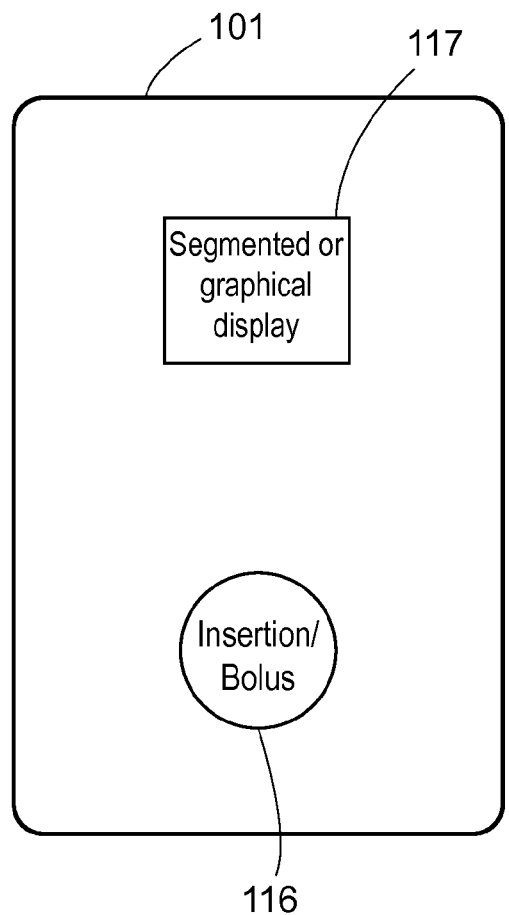
FIG. 1B is a top view of an alternative embodiment of the infusion pump housing having a graphical display.

FIG. 1B illustrates an embodiment of the device wherein the front side 101 of housing 100 is provided with the segmented or graphical display 117 alternative to the onboard LED display 105. The segmented or graphical display 117 comprises a display of digitally generated alphanumeric characters. The display 117 indicates the same information as the onboard display 105 detailed above, however, using alphanumeric characters instead of LEDs. For example, the display 117 will flash the words "ON", "SET BASAL", "FILL", "INSERT", and "STATUS" to indicate the information available to the user regarding status of the device and user prompts. The use of the segmented or graphical on-pump display 117 constitutes an alternative embodiment to the LED onboard display 105.

Figure 2A:
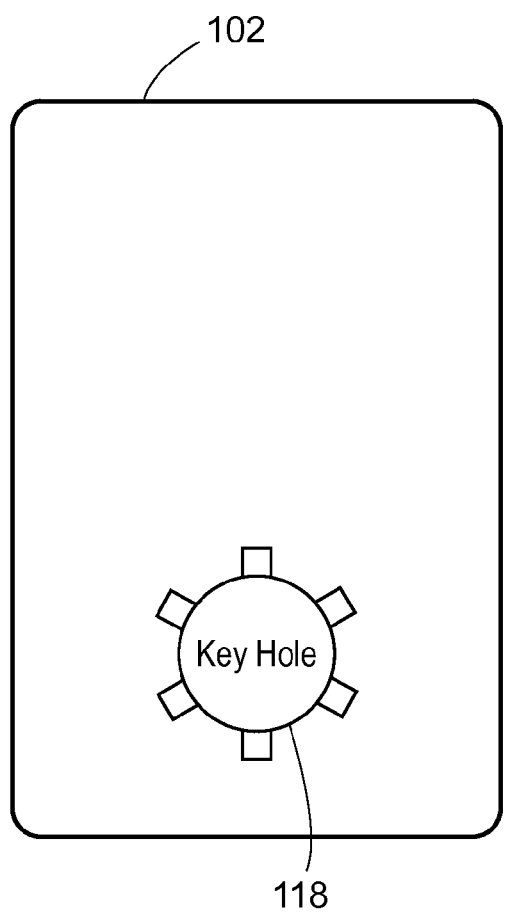
FIG. 2A is a bottom view of the infusion pump showing the program key insert aperture.
Figure 2B:
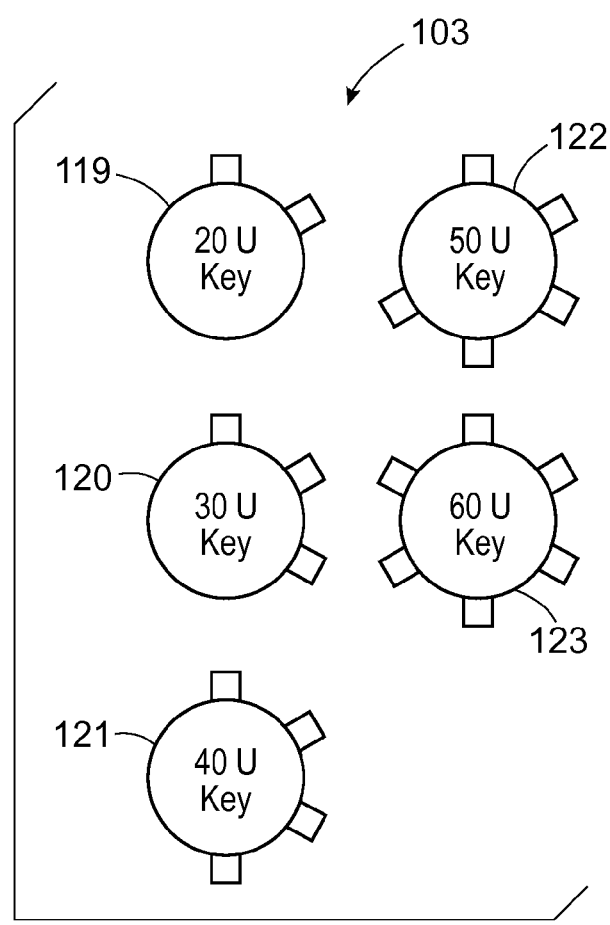
FIG. 2B is a schematic view of the program keys available for keying program information to the device.

An important aspect of the present invention is illustrated in FIGS. 2A and 2B which depict a program key insert aperture or "key hole" 118 which receives one of a plurality 103 of pre-programmed keys 119-123 each having a shape configured to close a predetermined number of contacts on printed circuit board (PCB) 133 which in turn communicates a predetermined instruction to microprocessor unit 130 to set the dosage. Using the pre-programmed keys allows the same pump to deliver different basal rates of insulin while at the same time avoiding the need for a complicated wireless programming device, which also reduces the likelihood of human error by eliminating the user calculation and programming steps characteristic of the prior art wireless devices.

FIG. 2A illustrates the bottom side 102 of the device where the program key insert aperture 118 is located. The bottom side of the housing 102 is sealed around the aperture 118 so that the device is water- and leak-proof. A flexible elastomeric material may be used for this purpose, sufficiently flexible to allow the program keys 119-123 to access the contacts on the PCB, but securely sealed against the opening. In embodiments, the microprocessor unit 130 is programmed to deliver a different dosage depending upon how many contacts are closed when the key is inserted, for example 10 units (U)/day, 20 U/day, 30 U/day up to 60 U/day. The contacts are depicted as extensions at different clock-hand positions extending radially from the perimeter of the key. Although many other configurations would be immediately apparent to those of ordinary skill in the art, this configuration is advantageous because a single stock keeping unit (SKU) is associated with the infusion pump capable of delivering different dosages depending on which key 119-123 is inserted, and the dosage programmed by the key is readily ascertained by the user simply by looking at the key, from its label, color, and/or shape.

The program keys are fashioned so that each different key closes a different number of contacts on the PCB. Each contact is connected to the microprocessor 130 through connecting traces 132. The number of closed connections indicates what the set basal rate is and how many units to administer. Thus, 2 closed contacts from the program key 119 to the key hole 118 indicates 20 U/day; 3 closed contacts from the program key 120 to the key hole 118 indicates 30 U/day, etc. The microprocessor unit 130, through connecting traces 132 on the PCB 133, communicates with actuator 127.

Figure 3:
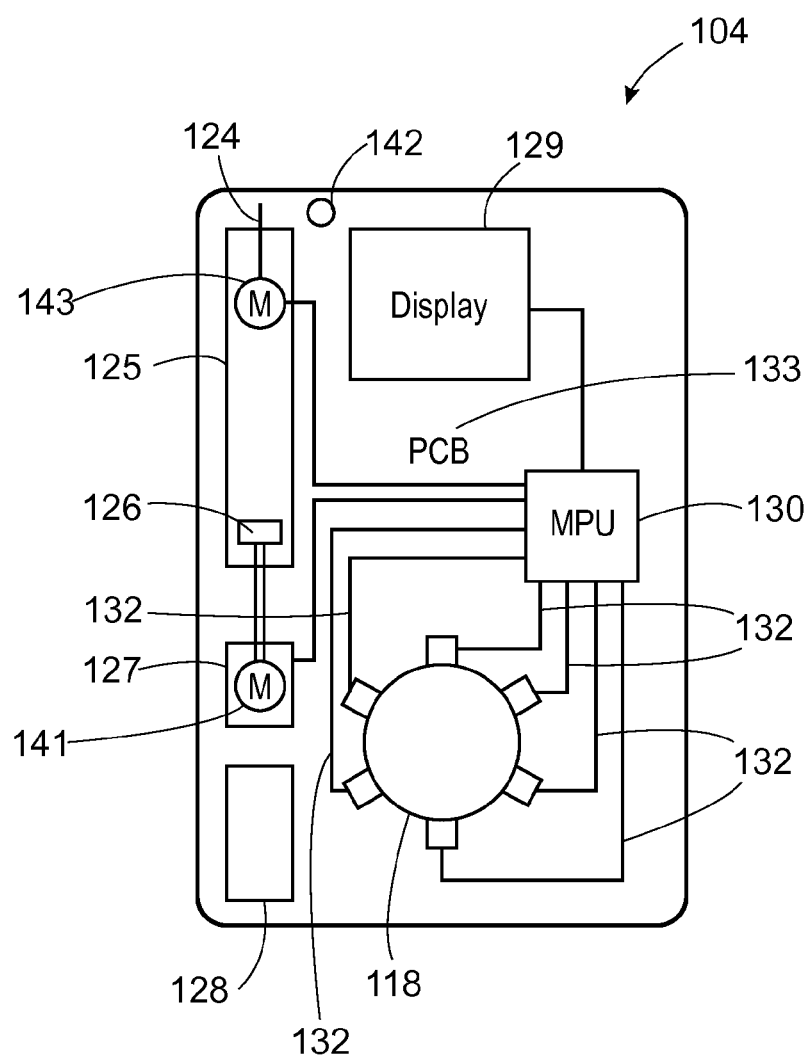
FIG. 3 is a cross-sectional, schematic view of an embodiment of the infusion pump.

FIG. 3 schematically portrays the internal elements 104 of the infusion pump where the contacts on the PCB 133 communicate with the microprocessor unit 130, which in turn communicates with the actuator 127, and the display 129 all of which are mounted on printed circuit board 133. The entire device is powered by an independent power source 128 housed in the device such as a battery or rechargeable battery.

In embodiments, the housing is provided with a single on-board user operable INSERTION/BOLUS button 116 for controlling cannula insertion and mealtime bolus delivery. The respective modes of the switch are dependent on the state of the device (i.e., the actuator cannot deliver a bolus unless the cannula has been inserted, and the cannula is only successfully inserted once). Alternatively, the device may be provided with separate insertion and bolus delivery buttons. After filling the reservoir, the user attaches infusion pump to the body, typically using an adhesive, and depresses the INSERTION/BOLUS 116 switch. Upon depression of the INSERTION/BOLUS 116 switch, the cannula 124 deploys from the housing 100 unit and breaks the user's skin. The cannula 124 then inserts into the subcutaneous layer of skin in order to deliver medication. The gauge of the cannula 124 must be such that it is small enough to be contained within the device and housing unit 100, however, it must be large enough also to prevent breakage and to continuously deliver the medication to the user. Therefore, a cannula with needle gauge of 25-29 is preferable.

The end of the cannula 124 opposite the point of insertion is in fluid communication with the reservoir 125. In embodiments, the reservoir 125 may be adapted to hold up to about 5 mL (500 U), corresponding to a maximum dosage delivered over a three day period, including mealtime bolus delivery, but more typically up to about 3 mL (300 U). In other embodiments, the pump is attached to an infusion set via tubing, so that the cannula is located on the infusion set.

The actuator 127 is also activated when the end-user pushes the INSERTION/BOLUS 116 button to deliver a one-time bolus of the drug. A preset amount of insulin is delivered each time the INSERTION/BOLUS button is depressed, such as 1 to 5 units, and typically 1, 2 or 3 units of insulin per depression, up to a predetermined maximum per day.

As described above, the actuator 127 is controlled through the MPU 130 by the number of closed contacts activated in the program key insert aperture 118 by the program key. The MPU 130 also controls the onboard display 105 or segmented or graphical display 117.

The foregoing description of the preferred embodiments is not to be deemed limiting of the invention, which is defined by the appended claims. The person of ordinary skill in the art, relying on the foregoing disclosure, may practice variants of the embodiments described without departing from the scope of the invention claimed. For example, although described in connection with continuous delivery of insulin for treatment of Type II diabetes, it will be apparent to those of skill in the art that the disposable pump could be adapted to deliver other medications. A feature or dependent claim limitation described in connection with one embodiment or independent claim may be adapted for use with another embodiment or independent claim, without departing from the scope of the invention.

What is claimed is:

1. A wearable infusion pump, comprising:
a housing having an on-board display, and within said housing
   an insertion cannula;
   a medication reservoir in fluid communication with the cannula;
   an actuator operatively communicating with the reservoir;
   a power source; and
   a microprocessor operatively communicating with the power source, the on-board display, the insertion cannula and the actuator;
said infusion pump further comprising
   a program key insert aperture in the housing sealed in a water-proof and leak-proof manner by a flexible elastomeric seal sealed around the program key insert aperture, the flexible elastomeric seal having sufficient flexibility to permit access to a plurality of contacts inside the housing, the aperture comprising six opening slots arranged radially around a central opening, the six opening slots adapted to receive a combination of key elements from a program key;
   the program key received in the program key insert aperture; and
   the plurality of contacts accessible by the program key being inserted through the program key insert aperture to be closed by the program key inserted in the program key insert aperture, the plurality of contacts operatively communicating with the microprocessor to set a dose rate for the infusion pump based on a number of the contacts on a printed circuit board closed by the inserted program key; wherein the program key closes one or more of the plurality of contacts while the elastomeric seal remains sealed to the program key insert aperture;
   wherein a number of the key elements of the program key corresponds to the number of the plurality of contacts closed when the program key is inserted into the program key insert aperture,
   wherein the microprocessor is programmed to set the dose rate corresponding to the number of the contacts closed by the program key; and
   wherein one contact of the plurality of contacts corresponds to a single key element of the key elements of the program key.

2. The wearable infusion pump according to claim 1, further comprising a user operable switch causing the insertion cannula to be inserted into a patient's subcutaneous tissue.

3. The wearable infusion pump according to claim 1, wherein the reservoir is sized to continuously deliver 10 to 80 units of insulin per day for three days.

4. The wearable infusion pump according to claim 1, wherein the on-board display comprises separate light emitting diodes indicating: (a) an ON/OFF state; (b) a fill state of the reservoir; (c) a basal rate set status; and (d) an error condition.

5. The wearable infusion pump according to claim 1, wherein the on-board display consists of digitally generated alphanumeric characters.

6. The wearable infusion pump according to claim 1, further comprising a user-operable switch to effect a bolus delivery.

7. The wearable infusion pump according to claim 1, comprising a single user-operable button effecting insertion of the insertion cannula and a bolus delivery.

8. The wearable infusion pump according to claim 1, adapted to deliver a continuous infusion of insulin over a period of three days for treatment of Type II diabetes.

9. The wearable infusion pump according to claim 1, wherein the infusion pump does not have a wireless receiver or transmitter element.

10. The wearable infusion pump according to claim 1, wherein the housing is provided with an adhesive element for direct attachment to a wearer's body.

11. The wearable infusion pump according to claim 1, wherein the housing is fluid-tight to prevent fluid ingress.

12. The wearable infusion pump according to claim 1, comprising a fill port on the housing in fluid communication with the reservoir.

13. The wearable infusion pump according to claim 1, wherein the reservoir is a replaceable cartridge.

14. A method of administering a continuous dose of insulin, comprising steps of:
   providing a wearable infusion pump, comprising a housing, and within said housing, an insertion cannula; a medication reservoir in fluid communication with the cannula; an actuator operatively communicating with the reservoir; an on-board display; a power source; a microprocessor operatively communicating with the power source, the on-board display, the insertion cannula and the actuator;
   inserting a program key into the housing through a program key insert aperture sealed in a water-proof and leak-proof manner by a flexible elastomeric seal sealed around the program key insert aperture, the flexible elastomeric seal having sufficient flexibility to permit access to a plurality of contacts inside the housing, the aperture comprising six opening slots arranged radially around a central opening, the six opening slots corresponding to key elements from the program key and the plurality of contacts, wherein the plurality of contacts are accessible to the inserted program key to close a plurality of the contacts corresponding to the inserted program key, and operatively communicating with the microprocessor to set a dose rate for the infusion pump;
   wherein a printed circuit board and the plurality of contacts are sealed relative to the program key insert aperture, the elastomeric seal being flexible to permit the program key to close one or more of the plurality of contacts when inserted into the program key insert aperture while the elastomeric seal remains sealed to the program key insert aperture;
   pressing an onboard user operable switch to cause insertion of the insertion cannula into a subcutaneous infusion site;
   wherein a number of the key elements of the program key corresponds to a number of the plurality of contacts closed when the program key is inserted into the program key insert aperture;
   setting the dose rate corresponding to the number of the contacts closed by the program key; and
   wherein one contact of the plurality of contacts corresponds to a single key element of the key elements of the program key.

15. The method according to claim 14, further comprising a step of pressing the onboard user operable switch to cause a mealtime bolus delivery of the insulin.

16. The method according to claim 14, further comprising a step of filling the reservoir with the insulin after inserting the program key into the housing responsive to an onboard display prompt.

17. The method according to claim 14, further comprising attaching the pump to a user's body with an adhesive.

18. The method according to claim 14, further comprising delivering a continuous dosage of 10 to 80 units per day of the insulin for three days and thereafter disposing of the pump.

19. A wearable medication infusion system, comprising:
   an infusion set comprising an insertion cannula;
   the infusion set connected by tubing to a wearable infusion pump, said pump comprising a housing having an on-board display, and within said housing
   a medication reservoir in fluid communication with the cannula;
   an actuator operatively communicating with the reservoir;
   a power source; and
   a microprocessor operatively communicating with the power source, the on-board display, the insertion cannula and the actuator;
   said infusion pump further comprising
      a program key insert aperture in the housing sealed in a water-proof and leak-proof manner by a flexible elastomeric seal sealed around the program key insert aperture, the flexible elastomeric seal having sufficient flexibility to permit access to a plurality of contacts inside the housing, the aperture comprising three or more six opening slots arranged radially around a central opening, the plurality of six opening slots adapted to receive a combination of key elements from a program key;
      the program key received in the program key insert aperture;
      a printed circuit board; and
      the plurality of contacts closed by the program key inserted in the program key insert aperture while the elastomeric seal remains sealed to the program key insert aperture,
   wherein the program key has a shape corresponding to one or more of the plurality of contacts to close one or more of the plurality of contacts when the program key is inserted into the program key insert aperture;
   wherein a number of the key elements of the program key corresponds to a number of the plurality of contacts closed when the program key is inserted into the program key insert aperture;
      the contacts operatively communicating with the microprocessor; wherein the microprocessor is programmed to set a dose rate for the infusion pump based on the number of the contacts closed by the inserted program key; and
   wherein one contact of the plurality of contacts corresponds to a single key element of the key elements of the program key.

\* \* \* \* \*